US00PP14702P2

(12) United States Plant Patent
Hansson

(10) Patent No.: US PP14,702 P2
(45) Date of Patent: Apr. 20, 2004

(54) SCHLUMBERGERA PLANT NAMED 'CEBELINA'

(50) Latin Name: *Schlumbergera bridgesii*
Varietal Denomination: Cebelina

(76) Inventor: Jorn Hansson, Holmevej 36, 5471 Sondersoe (DK)

( * ) Notice: Subject to any disclaimer, the term of this patent is extended or adjusted under 35 U.S.C. 154(b) by 0 days.

(21) Appl. No.: 10/396,534

(22) Filed: Mar. 25, 2003

(51) Int. Cl.[7] ..... A01H 5/00
(52) U.S. Cl. ..... Plt./372
(58) Field of Search ..... Plt./372

*Primary Examiner*—Bruce R. Campell
*Assistant Examiner*—Annette H Para
(74) *Attorney, Agent, or Firm*—C. A. Whealy

(57) ABSTRACT

A distinct cultivar of Schlumbergera plant named 'Cebelina', characterized by its compact, upright and outwardly spreading plant habit; short phylloclades; freely branching growth habit; and freely flowering with pale yellow-colored flowers.

2 Drawing Sheets

Botanical classification/cultivar designation: *Schlumbergera bridgesii* cultivar Cebelina.

BACKGROUND OF THE INVENTION

The present Invention relates to a new and distinct cultivar of Schlumbergera plant, botanically known as *Schlumbergera bridgesii*, and hereinafter referred to by the name 'Cebelina'.

The new Schlumbergera is a product of a planned breeding program conducted by the Inventor in Odense, Denmark. The objective of the breeding program is to create new compact Schlumbergeras with good postproduction longevity.

The new Schlumbergera originated from a cross-pollination in November, 1994, of two proprietary seedling selections of *Schlumbergera bridgesii*, not patented. The new Schlumbergera was discovered and selected as a single plant from the resulting progeny of the cross-pollination by the Inventor in a controlled environment in Odense, Denmark, on Nov. 10, 1996.

Asexual reproduction of the new cultivar by cuttings taken at Odense, Denmark, since Jan. 10, 1997, has shown that the unique features of this new Schlumbergera are stable and reproduced true to type in successive generations.

SUMMARY OF THE INVENTION

Plants of the cultivar Cebelina have not been observed under all possible environmental conditions. The phenotype may vary somewhat with variations in environment such as temperature and/or light intensity without, however, any variance in genotype.

The following traits have been repeatedly observed and are determined to be the unique characteristics of 'Cebelina'. These characteristics in combination distinguish 'Cebelina' as a new and distinct cultivar:

1. Compact, upright and outwardly spreading plant habit.
2. Short phylloclades.
3. Freely branching growth habit.
4. Freely flowering with pale yellow-colored flowers.

Plants of the new Schlumbergera differ from plants of the parent selections primarily in flower color as plants of the female, or seed, parent have white-colored flowers and plants of the male, or pollen, parent have orange-colored flowers.

Plants of the new Schlumbergera can be compared to plants of the cultivar Gold Charm, disclosed in U.S. Plant Pat. No. 5,104. In side-by-side comparisons conducted in Odense, Denmark, plants of the new Schlumbergera differed from plants of the cultivar Gold Charm in the following characteristics:

1. Plants of the new Schiumbergera had shorter and flatter phylloclades than plants of the cultivar Gold Charm.
2. Plants of the new Schiumbergera had shorter corolla tubes than plants of the cultivar Gold Charm.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Schlumbergera.

The photograph on the first sheet comprises a side perspective view of a typical plant of 'Cebelina'.

The photograph at the top of the second sheet comprises a close-up view of typical flowers of 'Cebelina'.

The photograph at the bottom of the sheet is a close-up view of developing flower buds and flowers of 'Cebelina'.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Odense, Denmark in 9-cm containers in a glass-covered greenhouse. During the production of the plants, day temperatures were about 18° C. and night temperatures were about 16 to 18° C. Plants used were about one year old when the photographs and description were taken.

Botanical classification: *Schlumbergera×haylodgensis* cultivar Cebelina.

Parentage:

*Female, or seed, parent.*—Proprietary seedling selection of *Schlumbergera bridgesii*, not patented.

*Male, or pollen, parent.*—Proprietary seedling selection of *Schlumbergera bridgesii*, not patented.

Propagation:

*Type.*—By cuttings.

*Time to initiate roots.*—Summer: About 10 days at 20° C. Winter: About 14 days at 18° C.

*Time to produce a rooted young plant.*—Summer: About 40 days at 20° C. Winter: About 50 days at 18° C.

*Root description.*—Fine; whitish in color.

Plant description:

*Form.*—Compact, upright and outwardly spreading; rounded inverted triangle.

*Branching habit.*—Freely branching with one to two phylloclades developing at the apex of each phylloclade.

*Plant height, soil level to top of plant plane.*—About 15 to 20 cm.

*Plant width.*—About 16 cm.

*Phylloclade description.*—Length: About 4 to 4.5 cm. Width: About 3 cm. Thickness: About 1 to 2 mm. Shape: Oblong to roughly vase-shaped. Apex: Truncated. Base: Obtuse. Margin: Serrate. Texture, upper and lower surfaces: Smooth, glabrous. Venation pattern: Pinnate. Color, upper and lower surfaces: 137A. Venation color, upper and lower surfaces: 137A.

Flower description:

*Flower type and habit.*—Single asymmetrical tubular flowers; flowers produced apically. Flowers persistent. Very freely flowering, typically about one to three flowers per terminal. Flowers not fragrant.

*Natural flowering season.*—Short day responsive; plants typically flower during November and December in Denmark; flowering recurrent.

*Flower longevity on the plant.*—About five days.

*Flower length.*—About 8.5 cm.

*Flower diameter.*—About 6.5 cm.

*Flower buds.*—Length: About 4 cm. Diameter: About 1.2 cm. Shape: Ovoid, pointed. Color: 12C.

*Corolla.*—Quantity/arrangement: About nine fused petals; funnelform. Petal length: About 4 cm. Petal width: About 1 to 1.5 cm. Petal shape: Oblong. Petal apex: Acute. Petal margin: Entire. Petal texture, upper and lower surfaces: Smooth, glabrous. Petal color, upper and lower surfaces: 12C to 14C. Petal color, lower surface:

*Reproductive organs.*—Stamens: Quantity per flower: About 40 to 50. Anther shape: Oblong. Anther length: About 5.5 cm. Anther color: 4C. Pollen amount: Abundant. Pollen color: 10A. Pistils: Quantity per flower: One. Pistil length: About 6.5 cm. Stigma shape: Rounded to oblong. Stigma color: 66B. Style length: About 5.8 cm. Style color: 66B. Ovary color: 147C.

*Seeds/fruit.*—Seed and fruit production has not been observed.

Disease/pest resistance: Under commercial production conditions, plants of the new Schlumbergera have not been noted to be resistant to pathogens or pests common to Schlumbergera.

Temperature tolerance: Plants of the new Schlumbergera have been observed to tolerate temperatures from about 2 to 30° C. in Odense, Denmark.

It is claimed:

1. A new and distinct cultivar of Schlumbergera plant named 'Cebelina', as illustrated and described.

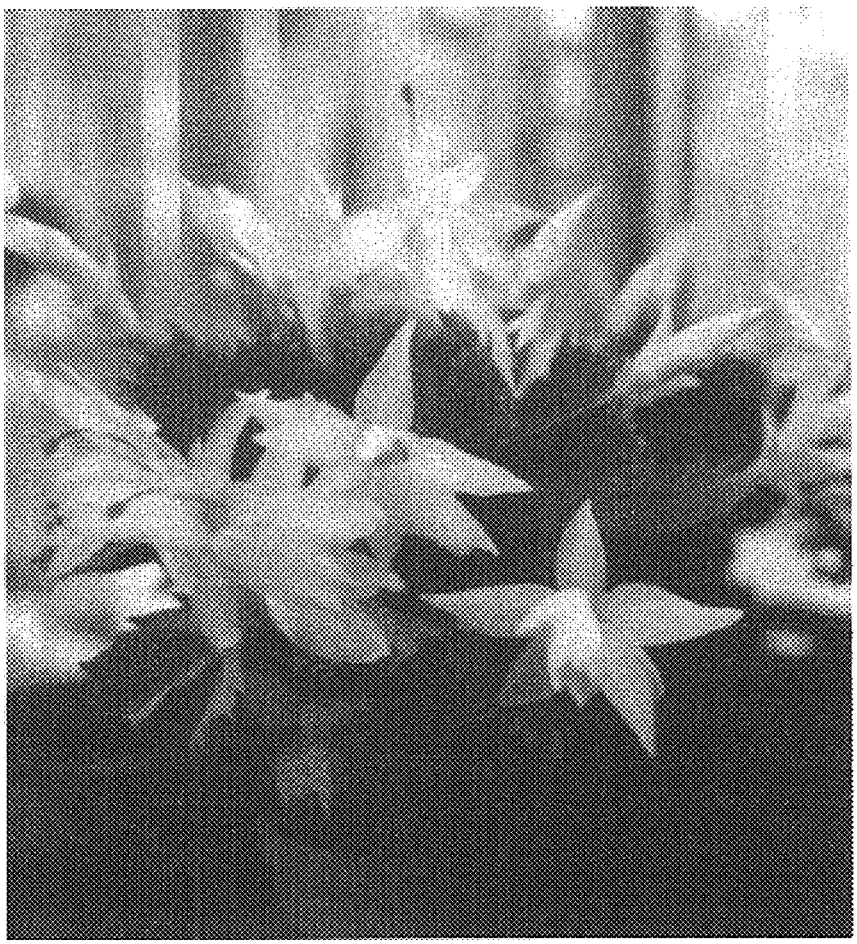

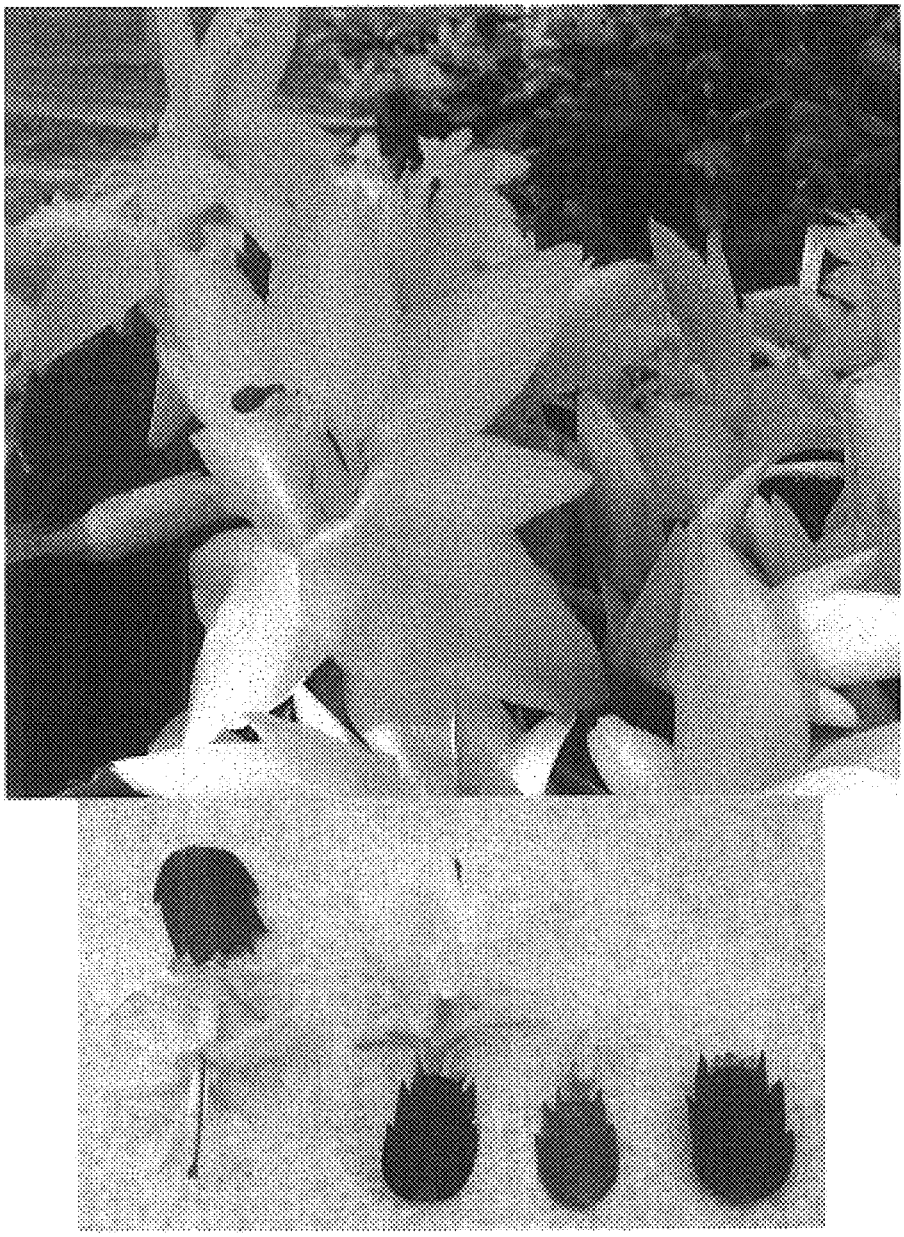

* * * * *